United States Patent
May

(10) Patent No.: US 10,172,747 B2
(45) Date of Patent: Jan. 8, 2019

(54) TOILET TRAINING ASSEMBLY

(71) Applicant: Brandy May, Calumet City, IL (US)

(72) Inventor: Brandy May, Calumet City, IL (US)

(*) Notice: Subject to any disclaimer, the term of this patent is extended or adjusted under 35 U.S.C. 154(b) by 385 days.

(21) Appl. No.: 14/923,639

(22) Filed: Oct. 27, 2015

(65) Prior Publication Data

US 2017/0112682 A1    Apr. 27, 2017

(51) Int. Cl.
| | |
|---|---|
| *A61F 13/15* | (2006.01) |
| *A61F 13/20* | (2006.01) |
| *A61F 13/496* | (2006.01) |
| *A61F 13/491* | (2006.01) |
| *A61F 13/49* | (2006.01) |

(52) U.S. Cl.
CPC ........ *A61F 13/496* (2013.01); *A61F 13/4915* (2013.01); *A61F 2013/49098* (2013.01)

(58) Field of Classification Search
CPC .......... A61F 13/496; A61F 2013/49098; A61F 13/471; A61F 13/505
See application file for complete search history.

(56) References Cited

U.S. PATENT DOCUMENTS

| | | | | |
|---|---|---|---|---|
| 3,974,836 A | * | 8/1976 | Carlson | A41C 1/003 2/408 |
| 4,446,575 A | * | 5/1984 | Davis | A41D 13/1254 2/400 |
| 4,637,078 A | * | 1/1987 | Southwell | A41B 9/007 2/408 |
| 4,835,795 A | * | 6/1989 | Lonon | A41B 9/007 2/408 |
| 4,944,733 A | | 7/1990 | Casale | |
| 5,569,229 A | * | 10/1996 | Rogers | A61F 13/42 604/358 |
| 5,636,387 A | * | 6/1997 | Lundy | A61F 5/0096 2/400 |
| 5,843,065 A | | 12/1998 | Wyant | |
| 5,930,838 A | * | 8/1999 | Carter-Scott-Pomije | A41D 1/06 2/227 |
| 6,102,899 A | * | 8/2000 | Yimin | A61F 13/84 604/385.01 |
| 6,213,992 B1 | * | 4/2001 | Dreier | A61F 13/42 604/385.01 |
| 6,324,699 B1 | * | 12/2001 | Cosmah | A41B 11/14 2/239 |
| D457,065 S | | 5/2002 | Krishnakumar et al. | |
| 6,412,119 B1 | * | 7/2002 | Robles | A41B 9/007 2/400 |
| D603,582 S | * | 11/2009 | Fennell | D2/712 |
| 8,696,642 B1 | | 4/2014 | Price | |
| 2005/0027280 A1 | | 2/2005 | Patty-Brown et al. | |
| 2013/0139303 A1 | | 6/2013 | Johnson | |

FOREIGN PATENT DOCUMENTS

WO    WO9611657    4/1996

* cited by examiner

*Primary Examiner* — Michele M Kidwell

(57) ABSTRACT

A toilet training assembly for training a toddler to urinate with the toddler's pants pulled up includes a diaper that may be worn thereby facilitating the diaper to capture human waste. The diaper has a flap thereon. The flap may be manipulated thereby facilitating a user to urinate in a toilet without removing the diaper.

7 Claims, 4 Drawing Sheets

TOILET TRAINING ASSEMBLY

BACKGROUND OF THE DISCLOSURE

Field of the Disclosure

The disclosure relates to training devices and more particularly pertains to a new training device for training a toddler to urinate with the toddler's pants pulled up.

SUMMARY OF THE DISCLOSURE

An embodiment of the disclosure meets the needs presented above by generally comprising a diaper that may be worn thereby facilitating the diaper to capture human waste. The diaper has a flap thereon. The flap may be manipulated thereby facilitating a user to urinate in a toilet without removing the diaper.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
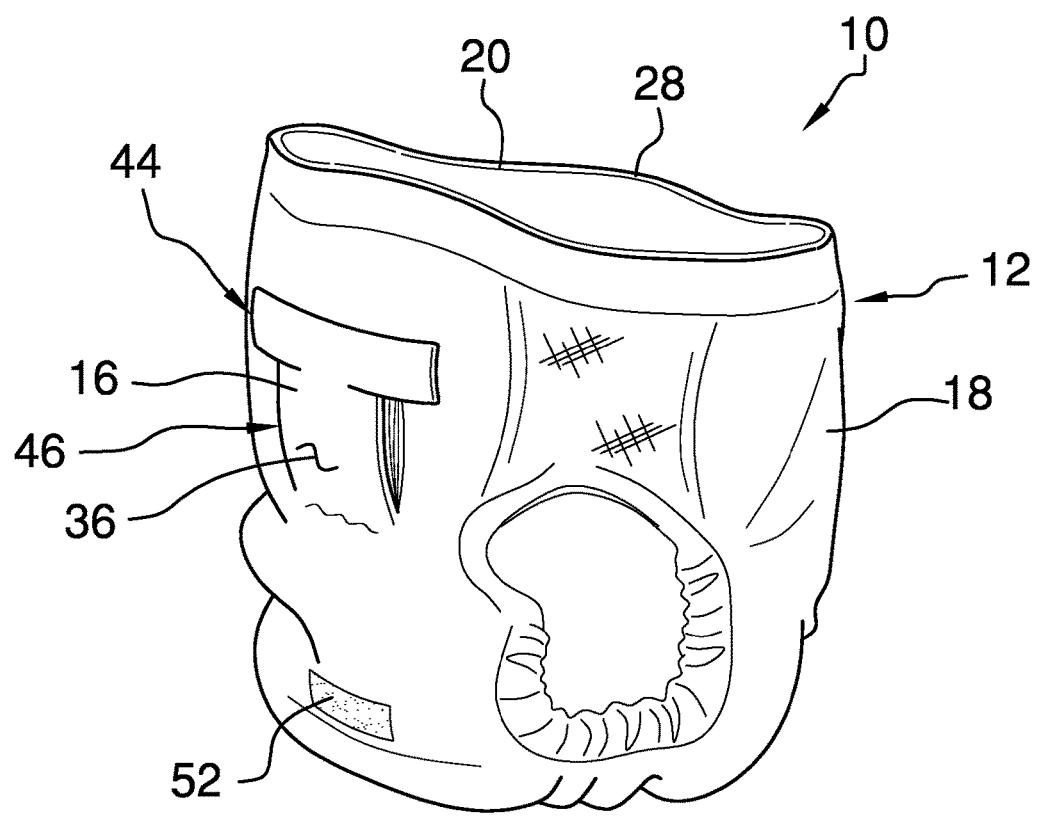
FIG. 1 is a perspective view of a toilet training assembly according to an embodiment of the disclosure.
Figure 2:
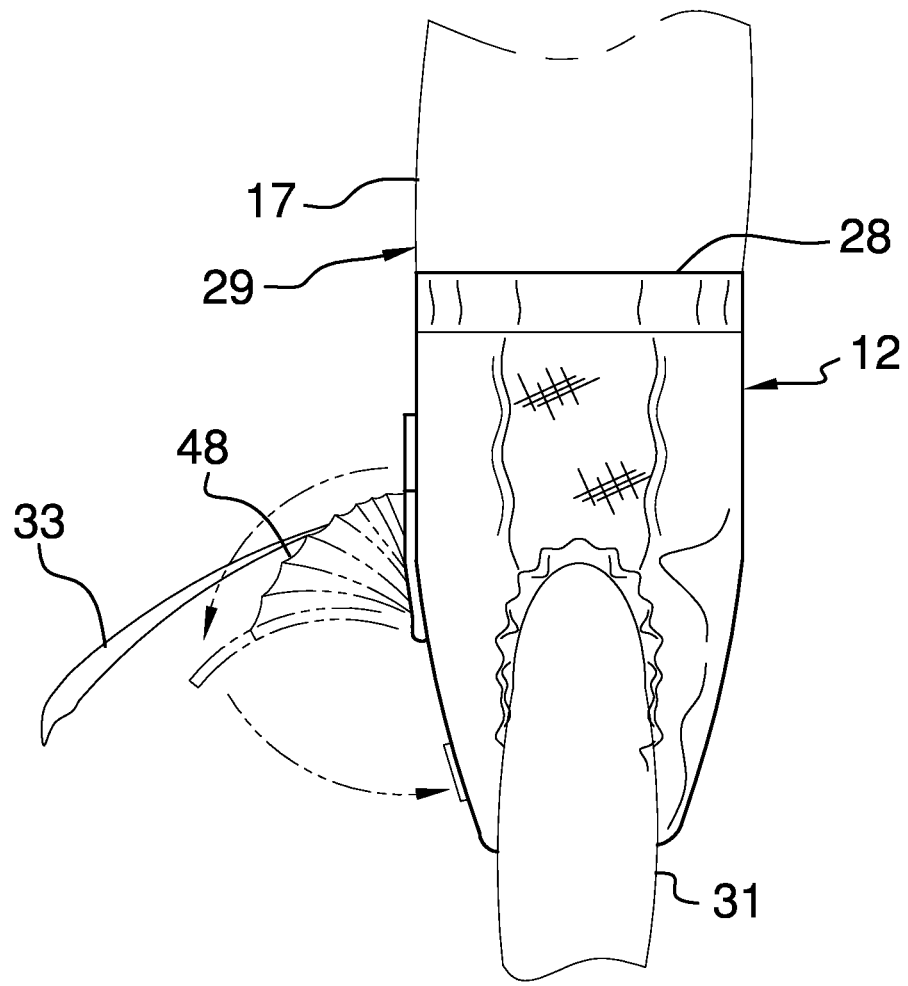
FIG. 2 is a perspective in-use view of an embodiment of the disclosure.
Figure 3:
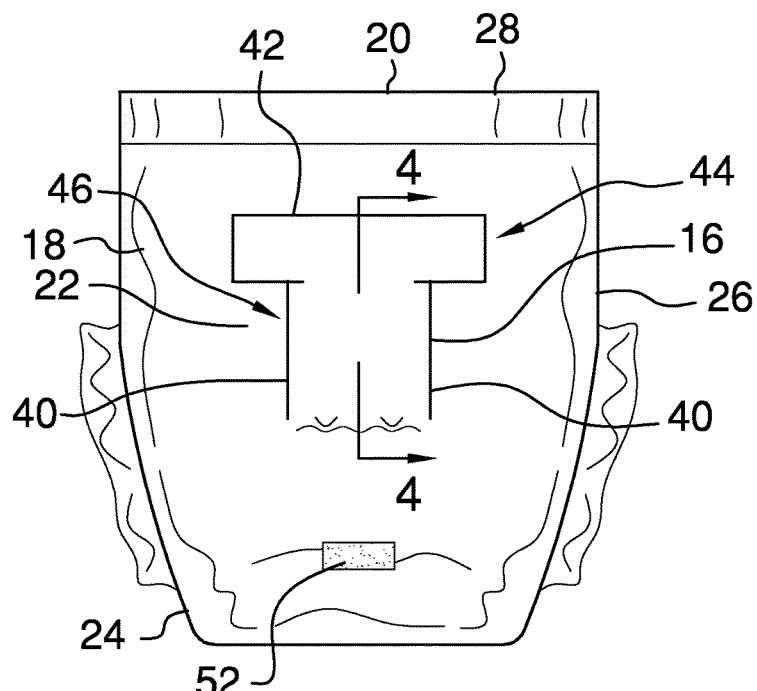
FIG. 3 is a front view of an embodiment of the disclosure.
Figure 4:
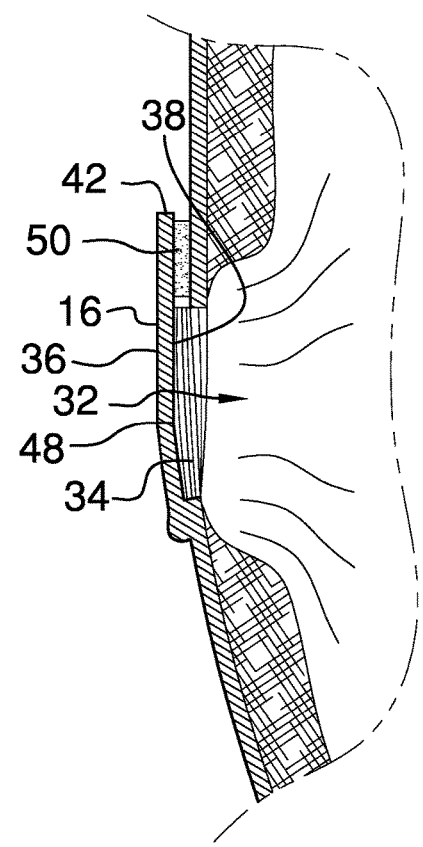
FIG. 4 is a cross sectional view taken along line 4-4 of FIG. 3 of an embodiment of the disclosure.
Figure 5:
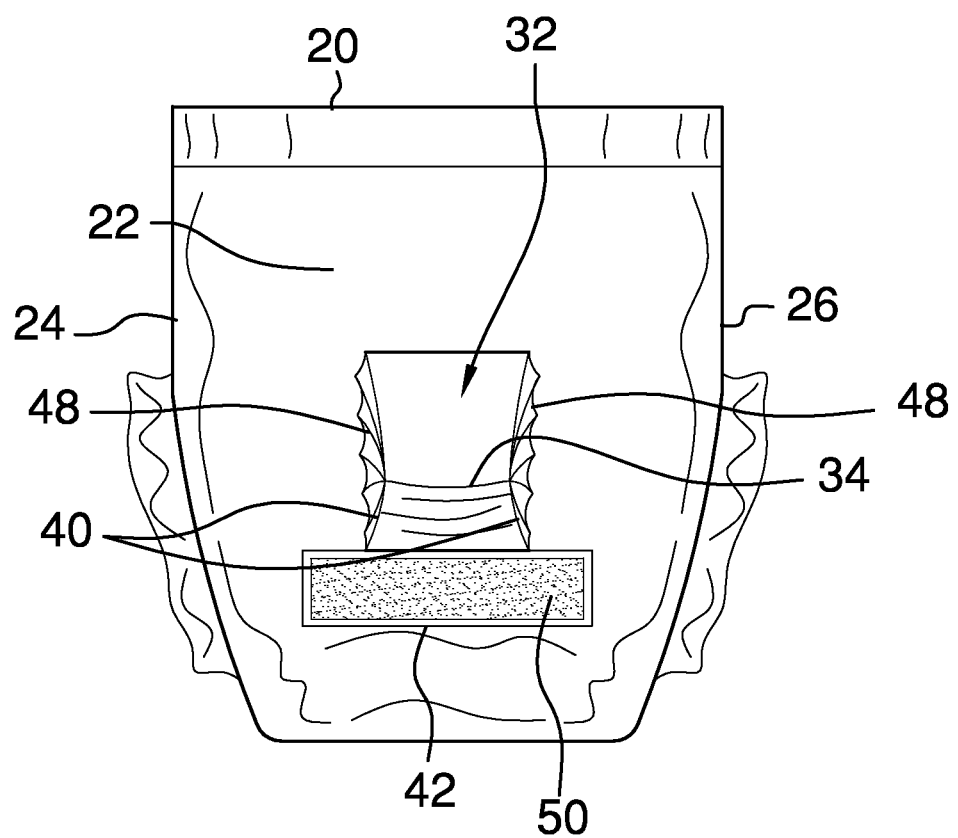
FIG. 5 is a front perspective view of an embodiment of the disclosure.

With reference now to the drawings, and in particular to FIGS. 1 through 5 thereof, a new training device embodying the principles and concepts of an embodiment of the disclosure and generally designated by the reference numeral 10 will be described.

As best illustrated in FIGS. 1 through 5, the toilet training assembly 10 generally comprises a diaper 12 that may be worn thereby facilitating the diaper 12 to capture human waste 14. The diaper 12 has a flap 16 thereon. The flap 16 may be manipulated to facilitate a user 17 to urinate in a toilet without removing the diaper 12. The user 17 may be a toddler that is being toilet trained.

The diaper 12 has an outer wall 18. The outer wall 18 has a top edge 20, a front side 22, a first lateral side 24 and a second lateral side 26. The top edge 20 is continuous to define waistband 28 of the diaper 12. The outer wall 18 has a pair of leg openings 30 extending therethrough. The top edge 20 extends around a waist 29 of the user 17 and each of the user's legs 31 extends through an associated one of the leg openings 30.

The outer wall 18 has an aperture 32 extending therethrough. The aperture 32 is centrally positioned on the front side 22 such that the aperture 32 may have urine 33 pass therethrough. The aperture 32 has a lower bounding edge 34. The flap 16 has a front surface 36, a back surface 38, a pair of lateral edges 40 and an upper edge 42. The flap 16 has a grip portion 44 and a body portion 46. The grip portion 44 extends along the top edge 20. The grip portion 44 has a width that is greater than a width of the body portion 46 such that the grip portion 44 may be gripped.

The flap 16 is movably coupled to the lower bounding edge 34. The flap 16 is positioned in a covering position having the flap 16 closing the aperture 32. The flap 16 is positioned in an open position. The aperture 32 is exposed thereby facilitating the user 17 to urinate through the aperture 32.

A pair of guards 48 is provided and each of the guards 48 is coupled between the flap 16 and the front side 22 of the diaper 12. Each of the guards 48 is aligned with an associated one of the lateral edges 40 corresponding to the body portion 46. Each of the guards 48 is pleated such that each of the guards 48 is collapsed between the flap 16 and the diaper 12 when the flap 16 is positioned on the covering position. Each of the guards 48 extends between the flap 16 and the diaper 12 when the flap 16 is positioned in the open position. Thus, each of the guards 48 inhibits the urine 33 from splashing laterally from the aperture 32.

A first adhesive layer 50 is coupled the flap 16. The first adhesive layer 50 is positioned on the back surface 38 corresponding to grip portion 44. The first adhesive layer 50 adhesively engages the outer wall 18 when the flap 16 is positioned in the covering position. Thus, the flap 16 is removably retained in the covering position.

A second adhesive layer 52 is coupled to the outer wall 18. The second adhesive layer 52 is positioned below the flap 16. The second adhesive layer 52 adhesively engages the front surface 36 of the flap 16 when the flap 16 is positioned in the open position. Thus, the flap 16 is removably retained in the open position.

In use, the diaper 12 is worn by the user 17 while the user 17 is toilet training. The flap 16 is positioned in the open position when the user 17 wishes to urinate in the toilet. Thus, the user 17 does not have to remove the diaper 12 to urinate in the toilet. The flap 16 is positioned in the covering position when the user 17 is finished urinating. The diaper 12 trains the user 17 to leave the user's pants pulled up while the user 17 urinates.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A toilet training assembly comprising:
a diaper being configured to be worn thereby facilitating said diaper to capture human waste said diaper having an outer wall, said outer wall having a top edge, a front side, a first lateral side and a second lateral side, said top edge being continuous to define a waistband of said diaper, said outer wall having a pair of leg openings extending therethrough, said top edge being configured to extend around a waist of the user having each of the user's legs extending through an associated one of said leg openings, said outer wall having an aperture extending therethrough, said aperture being centrally positioned on said front side wherein said aperture is configured have urine pass therethrough, said aperture having a lower bounding edge, said diaper having a flap thereon selectively positionable to cover said aperture wherein said flap is configured to be manipulated to permit urination through said aperture;
a first adhesive layer being coupled said flap, said first adhesive layer adhesively engaging said outer wall over said aperture when said flap is positioned in a covering position such that said flap is removably retained in said covering position; and
a second adhesive layer being coupled to said outer wall, said second adhesive layer being positioned below said flap, said second adhesive layer adhesively engaging said front surface of said flap when said flap is positioned in an open position such that said flap is removably retained in said open position.

2. The assembly according to claim 1, wherein said flap has a front surface, a back surface, a pair of lateral edges and an upper edge, said flap having a grip portion and a body portion, said grip portion extending along said top edge, said grip portion having a width being greater than a width of said body portion wherein said grip portion is configured to be gripped.

3. The assembly according to claim 1, wherein said flap is movably coupled to said lower bounding edge such that said flap is positioned in said covering position having said flap closing said aperture, said flap being positioned in said open position having said aperture being exposed thereby facilitating urination through said aperture.

4. The assembly according to claim 1, further comprising a pair of guards, each of said guards being coupled between said flap and said front side, each of said guards being aligned with an associated one of said lateral edges corresponding to said body portion.

5. The assembly according to claim 4, wherein each of said guards being pleated such that each of said guards is collapsed between said flap and said diaper when said flap is positioned on said covering position, each of said guards extending between said flap and said diaper when said flap is positioned in said open position wherein each of said guards is configured to inhibit the urine from splashing laterally from an aperture.

6. The assembly according to claim 2, further comprising:
said diaper having an outer wall; and
said first adhesive layer being positioned on said back surface corresponding to grip portion.

7. A toilet training assembly comprising:
a diaper being configured to be worn thereby facilitating said diaper to capture human waste, said diaper having a flap thereon wherein said flap is configured to be manipulated thereby facilitating a user to urinate in a toilet without removing said diaper, said diaper having an outer wall, said outer wall having a top edge, a front side, a first lateral side and a second lateral side, said top edge being continuous to define a waistband of said diaper, said outer wall having a pair of leg openings extending therethrough, said top edge being configured to extend around a waist of the user having each of the user's legs extending through an associated one of said leg openings, said outer wall having an aperture extending therethrough, said aperture being centrally positioned on said front side wherein said aperture is configured have urine pass therethrough, said aperture having a lower bounding edge, said flap having a front surface, a back surface, a pair of lateral edges and an upper edge, said flap having a grip portion and a body portion, said grip portion extending along said top edge, said grip portion having a width being greater than a width of said body portion wherein said grip portion is configured to be gripped, said flap being movably coupled to said lower bounding edge such that said flap is positioned in a covering position having said flap closing said aperture, said flap being positioned in an open position having said aperture being exposed thereby facilitating the user to urinate through said aperture;
a pair of guards, each of said guards being coupled between said flap and said front side, each of said guards being aligned with an associated one of said lateral edges corresponding to said body portion, each of said guards being pleated such that each of said guards is collapsed between said flap and said diaper when said flap is positioned on said covering position, each of said guards extending between said flap and said diaper when said flap is positioned in said open position wherein each of said guards is configured to inhibit the urine from splashing laterally from said aperture;
a first adhesive layer being coupled said flap, said first adhesive layer being positioned on said back surface corresponding to grip portion, said first adhesive layer adhesively engaging said outer wall when said flap is positioned in said covering position such that said flap is removably retained in said covering position; and
a second adhesive layer being coupled to said outer wall, said second adhesive layer being positioned below said flap, said second adhesive layer adhesively engaging said front surface of said flap when said flap is positioned in said open position such that said flap is removably retained in said open position.

* * * * *